United States Patent
Osanishi

(10) Patent No.: US 10,906,332 B2
(45) Date of Patent: Feb. 2, 2021

(54) PRETREATMENT SOLUTION FOR INKJET RECORDING, INKJET RECORDING APPARATUS, AND IMAGE FORMING METHOD

(71) Applicant: KYOCERA Document Solutions Inc., Osaka (JP)

(72) Inventor: Katsuki Osanishi, Osaka (JP)

(73) Assignee: KYOCERA Document Solutions Inc., Osaka (JP)

( * ) Notice: Subject to any disclaimer, the term of this patent is extended or adjusted under 35 U.S.C. 154(b) by 0 days.

(21) Appl. No.: 16/512,634

(22) Filed: Jul. 16, 2019

(65) Prior Publication Data
US 2020/0024470 A1 Jan. 23, 2020

(30) Foreign Application Priority Data
Jul. 19, 2018 (JP) .................................. 2018-135834

(51) Int. Cl.
*B41J 11/00* (2006.01)
*C09D 11/54* (2014.01)
*C07C 309/71* (2006.01)

(52) U.S. Cl.
CPC ........... *B41J 11/002* (2013.01); *C07C 309/71* (2013.01); *C09D 11/54* (2013.01); *C07C 2601/16* (2017.05); *C07C 2602/42* (2017.05)

(58) Field of Classification Search
CPC ....... C09D 11/54; C09D 11/322; C09D 11/36; C09D 11/40; C09D 11/30; C09D 11/38;
(Continued)

(56) References Cited

U.S. PATENT DOCUMENTS 7,338,143 B2   3/2008  Onishi et al.
2001/0026904 A1* 10/2001  Nishi ................... C08F 232/08
                                                                                          430/296
(Continued)

FOREIGN PATENT DOCUMENTS

JP          2002-019263 A       1/2002
JP          2003-055886 A       2/2003
WO         2003/043825 A1       5/2003

*Primary Examiner* — Manish S Shah
(74) *Attorney, Agent, or Firm* — Studebaker & Brackett PC

(57) ABSTRACT

A pretreatment solution for inkjet recording contains a photoacid generator that generates sulfonic acid through light exposure. The photoacid generator may be a compound represented by a general formula (I) or (II), wherein $R^1$ represents a substituted or unsubstituted alkyl group, a substituted or unsubstituted cycloalkyl group, a substituted or unsubstituted aryl group, a substituted or unsubstituted heterocyclic group, a fluorine atom, a nitro group, or a cyano group; and $R^2$ represents a hydrogen atom, a substituted or unsubstituted alkyl group, a substituted or unsubstituted alkenyl group, a substituted or unsubstituted alkynyl group, a substituted or unsubstituted cycloalkyl group, a substituted or unsubstituted cycloalkenyl group, a substituted or unsubstituted cycloalkynyl group, a substituted or unsubstituted aryl group, a substituted or unsubstituted heterocyclic group, an acylamide group, a sulfonylamide group, or a halogen atom (Continued)

-continued

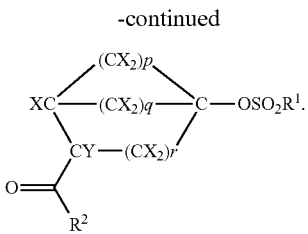

(II)

7 Claims, 1 Drawing Sheet

(58) Field of Classification Search
CPC ..... C09D 11/32; C09D 11/324; C09D 11/328; C09D 11/101; C09D 11/102; C09D 11/005; C09D 11/52; C09D 11/106; C09D 11/326; C09D 11/107; C09D 11/03; C09D 11/037; C09D 11/033; C07C 309/71; C07C 2602/42; C07C 2601/16; C07C 309/65; B41J 11/002; B41J 11/0015; B41J 2/01; B41J 2/211; B41J 2/0057; B41J 2/1433; B41J 2/045; B41J 2/16538; B41J 2002/16502; B41J 29/02; B41J 2/17513; B41J 2/17509; B41J 29/13; B41J 2/17553; B41J 2/1606; B41J 2/1642; B41J 2/1609; B41J 2/164; B41J 2/162; B41J 2/17; B41J 2/17593; B41J 2/2107; B41J 2/1755; B41J 2/2114; B41J 2/2117; B41J 2/2056; B41J 2/21; B41J 3/60; B41J 2002/012; B41J 2/04598; B41J 2/1623; B41J 2202/00; B41J 2202/03; B41J 2/14201; B41J 2/04581; B41J 2/055; B41J 2/161; B41J 2/19; B41J 15/04
See application file for complete search history.

(56) References Cited

U.S. PATENT DOCUMENTS

| | | | | |
|---|---|---|---|---|
| 2001/0041300 A1* | 11/2001 | Kodama | ............... | G03F 7/039 430/170 |
| 2002/0094490 A1* | 7/2002 | Endo | ............... | B41N 1/08 430/278.1 |
| 2002/0098440 A1* | 7/2002 | Sato | ............... | G03F 7/0397 430/270.1 |
| 2002/0197558 A1* | 12/2002 | Ferreira | ............... | C07C 381/12 430/270.1 |
| 2003/0027061 A1* | 2/2003 | Cameron | ............... | C07C 303/20 430/14 |
| 2003/0057610 A1* | 3/2003 | Kunita | ............... | B41C 1/1008 264/401 |
| 2005/0003299 A1* | 1/2005 | Adegawa | ............... | C09D 183/14 430/270.1 |
| 2005/0175927 A1* | 8/2005 | Kishioka | ............... | G03F 7/091 430/270.1 |
| 2005/0243121 A1 | 11/2005 | Onishi | | |
| 2009/0246694 A1* | 10/2009 | Ohsawa | ............... | C07C 309/12 430/285.1 |
| 2010/0075061 A1* | 3/2010 | Yokoi | ............... | C09D 11/101 427/487 |
| 2015/0118623 A1* | 4/2015 | Tsuruta | ............... | C08F 212/14 430/286.1 |

* cited by examiner

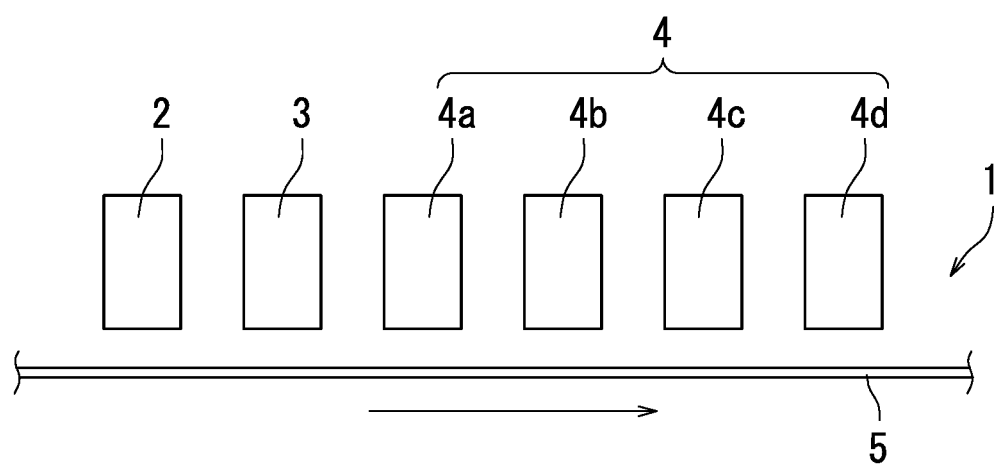

PRETREATMENT SOLUTION FOR INKJET RECORDING, INKJET RECORDING APPARATUS, AND IMAGE FORMING METHOD

INCORPORATION BY REFERENCE

The present application claims priority under 35 U.S.C. § 119 to Japanese Patent Application No. 2018-135834, filed on Jul. 19, 2018. The contents of this application are incorporated herein by reference in their entirety.

BACKGROUND

The present disclosure relates to a pretreatment solution for inkjet recording, an inkjet recording apparatus, and an image forming method.

An inkjet recording apparatus is required, by a line-engine system for commercial printing use, to realize image quality as high as that of known offset printing on coated paper for printing. In such use, it is significant to improve dot reproducibility with curl of a recording medium and strike-through of an ink inhibited. Besides, in on-demand printing, POP (point of purchase) advertisement, and sign graphics market, demands for a technique for forming a high quality image using an inkjet recording apparatus on a recording medium of a transparent film wholly coated with a white coating material are rapidly increasing. In such use, it is required to form an image having high image quality and excellent in fastness on a recording medium poor in absorption.

In order to meet such requirements, for example, a method in which a recording medium is precedently pretreated, a method in which a recording medium is heated immediately after printing, a method in which a fast-drying ink is used, and a method in which a UV curing ink is used have been examined. In employing the method in which a recording medium is precedently pretreated, however, time and cost tend to increase due to increase of the number of processes. Besides, in employing the method in which a recording medium is heated immediately after printing, or a method in which a fast-drying ink is used, ink nozzles tend to be easily clogged. Furthermore, in employing the method in which a UV curing ink is used, the ink may be cured before the ejected ink is sufficiently flattened in some cases. Therefore, in employing the method in which a UV curing ink is used, irregularities tend to be formed on a surface of a printed image, and in addition, the thickness of an ink layer thus formed tends to increase.

Therefore, a method in which a pretreatment solution for inkjet recording is ejected onto a recording medium immediately before ejecting an ink with a member for ejecting the pretreatment solution provided in an inkjet recording apparatus has been proposed. As examples of an active ingredient of the pretreatment solution for inkjet recording, for example, a cationic polymer compound, an acid component and a metal ion have been proposed. When the pretreatment solution for inkjet recording containing such an active ingredient is used, an aggregation reaction of the active ingredient and a pigment contained in the ink is caused on the surface of a recording medium, resulting in accelerating fixation of the pigment on the recording medium. Thus, image quality of an image to be formed is presumed to be improved.

SUMMARY

A pretreatment solution for inkjet recording according to the present disclosure contains a photoacid generator that generates sulfonic acid through light exposure.

An inkjet recording apparatus according to the present disclosure is an inkjet recording apparatus for forming an image in an image forming region on a recording medium, and includes a pretreating section configured to eject the pretreatment solution for inkjet recording onto the image forming region on the recording medium; an exposing section configured to expose to light the image forming region on the recording medium on which the pretreatment solution for inkjet recording has been ejected; and a recording head configured to form the image by ejecting an ink onto the exposed image forming region on the recording medium.

An image forming method according to the present disclosure is a method for forming an image in an image forming region on a recording medium, and includes ejecting the pretreatment solution for inkjet recording onto the image forming region on the recording medium; exposing to light the image forming region on the recording medium on which the pretreatment solution for inkjet recording has been ejected; and forming the image by ejecting an ink onto the exposed image forming region on the recording medium.

BRIEF DESCRIPTION OF THE DRAWING

FIGURE is a side view of a principal part of an example of an inkjet recording apparatus according to a second embodiment of the present disclosure.

DETAILED DESCRIPTION

Now, embodiments of the present disclosure will be described in detail. The present disclosure is, however, not limited to the following embodiments at all. The present disclosure can be practiced with appropriate modification made within the scope of the object of the present disclosure. It is noted that description will be appropriately omitted in some cases for avoiding redundant description, which does not limit the spirit of the disclosure. In the accompanying drawing, dimensional relationship in the length, the width, the thickness, the depth and the like is appropriately modified for clarifying and simplifying the drawing, and does not indicate the actual dimensional relationship. In regard to each component, one type of the component may be singly used, or two or more types may be used in combination unless otherwise stated.

In the following description, the term "-based" is appended, in some cases, to the name of a chemical compound to be used as a generic name encompassing both the chemical compound and derivatives thereof. When the term "-based" is appended to the name of a chemical compound used in the name of a polymer, the term indicates that a repeating unit of the polymer originates from the chemical compound or a derivative thereof. Furthermore, the term "(meth)acryl" may be used as a generic term encompassing both acryl and methacryl.

In the following description, a halogen atom, an alkyl group, an alkenyl group, an alkynyl group, a cycloalkyl group, a cycloalkenyl group, a cycloalkynyl group, an alkoxy group, an aryl group, and a heterocyclic group respectively have the following meanings unless otherwise stated.

Examples of the halogen atom (halogen group) include a fluorine atom (fluoro group), a chlorine atom (chloro group), a bromine atom (bromo group), and an iodine atom (iodo group).

The alkyl group is straight or branched, and unsubstituted. The alkyl group has a carbon number of, for example, at least 1 and no greater than 20. Examples of the alkyl group having a carbon number of at least 1 and no greater than 20 include a methyl group, an ethyl group, an n-propyl group, an isopropyl group, an n-butyl group, a sec-butyl group, a tert-butyl group, an n-pentyl group, an isopentyl group, a neopentyl group, a 1,2-dimethylpropyl group, a straight or branched hexyl group, a straight or branched heptyl group, a straight or branched octyl group, a straight or branched nonyl group, a straight or branched decyl group, and a straight or branched icosyl group.

The alkenyl group and the alkynyl group are straight or branched, and unsubstituted. Each of the alkenyl group and the alkynyl group has a carbon number of, for example, at least 2 and no greater than 20. Examples of the alkenyl group having a carbon number of at least 2 and no greater than 20 include an ethenyl group, a propenyl group, a butenyl group, a pentenyl group, a hexenyl group, a heptenyl group, an octenyl group, a nonenyl group, a decenyl group, a pentadecenyl group, and an icosenyl group. Examples of the alkynyl group having a carbon number of at least 2 and no greater than 20 include an ethynyl group, a propynyl group, a butynyl group, a pentynyl group, a hexynyl group, a heptynyl group, an octynyl group, a nonynyl group, a decynyl group, and an icosynyl group.

The cycloalkyl group is unsubstituted. The cycloalkyl group has a carbon number of, for example, at least 3 and no greater than 20. Examples of the cycloalkyl group having a carbon number of at least 3 and no greater than 20 include a cyclopropyl group, a cyclobutyl group, a cyclopentyl group, a cyclohexyl group, a cycloheptyl group, a cyclooctyl group, a cyclononyl group, a cyclodecyl group, a cycloundecyl group, cyclododecyl group, a cyclotridecyl group, a cyclotetradecyl group, a cyclopentadecyl group, a cyclohexadecyl group, a cyclooctadecyl group, a cyclononadecyl group, and a cycloicosyl group.

The cycloalkenyl group and the cycloalkynyl group are unsubstituted. An example of the cycloalkenyl group includes a group obtained by substituting, in any of the above-described cycloalkyl groups, at least one carbon-carbon bond by a carbon-carbon double bond. An example of the cycloalkynyl group includes a group obtained by substituting, in any of the above-described cycloalkyl groups, at least one carbon-carbon bond by a carbon-carbon triple bond.

The alkoxy group is straight or branched, and unsubstituted. The alkoxy group has a carbon number of, for example, at least 1 and no grater than 20. Examples of the alkoxy group having a carbon number of at least 1 and no greater than 20 include a methoxy group, an ethoxy group, an n-propoxy group, an isopropoxy group, an n-butoxy group, an isobutoxy group, a sec-butoxy group, a tert-butoxy group, an n-pentyloxy group, an n-hexyloxy group, an n-heptyloxy group, an n-octyloxy group, an n-nonyloxy group, and an n-decyloxy group.

The aryl group is unsubstituted. The aryl group has a carbon number of, for example, at least 6 and no greater than 14. Examples of the aryl group having a carbon number of at least 6 and no greater than 14 include a phenyl group, a naphthyl group, an indacenyl group, a biphenylenyl group, an acenaphthylenyl group, an anthryl group, and a phenanthryl group.

The heterocyclic group is a monovalent unsubstituted group, and contains, for example, a carbon atom and a hetero atom (for example, at least one of a nitrogen atom, a sulfur atom, and an oxygen atom). The number of ring members of the heterocyclic group is, for example, at least 3 and no greater than 20. Specific examples of the heterocyclic group having at least 3 and no greater than 20 ring members include a piperidinyl group, a piperazinyl group, a morpholinyl group, a thiophenyl group, a furanyl group, a pyrrolyl group, an imidazolyl group, a pyrazolyl group, an isothiazolyl group, an isooxazolyl group, an oxazolyl group, a thiazolyl group, a furazanyl group, a pyranyl group, a pyridyl group, a pyridazinyl group, a pyrimidinyl group, a pyradinyl group, an indolyl group, a 1H-indazolyl group, an isoindolyl group, a chromenyl group, a quinolinyl group, an isoquinolinyl group, a purinyl group, a pteridinyl group, a triazolyl group, a tetrazolyl group, a 4H-quinolidinyl group, a naphthyridinyl group, a benzofuranyl group, a 1,3-benzodioxolyl group, a benzoxazolyl group, a benzothiazolyl group, a benzimidazolyl group, a carbazolyl group, a phenanthridinyl group, an acridinyl group, a phenazinyl group, and a phenanthrolinyl group.

A measured value of a volume median diameter ($D_{50}$) of a powder (for example, pigment dispersing elements) is a value measured using a laser diffraction particle size distribution measuring apparatus ("ZETASIZER nano-ZS" manufactured by Malvern) unless otherwise stated.

First Embodiment: Pretreatment Solution for Inkjet Recording

A pretreatment solution for inkjet recording according to a first embodiment of the present disclosure (hereinafter sometimes referred to as the pretreatment solution) contains a photoacid generator that generates sulfonic acid through light exposure (hereinafter sometimes referred to as the photoacid generator). The pretreatment solution preferably further contains, as a solvent, water and a water-soluble organic solvent in addition to the photoacid generator. The pretreatment solution may further contain a surfactant as an optional component. The pretreatment solution may further contain an additional component if necessary.

An example of usage of the pretreatment solution of the present embodiment will now be described. First, in image formation using an inkjet recording apparatus, immediately before forming an image in an image forming region on a recording medium by ejecting an ink, the pretreatment solution is ejected onto the image forming region on the recording medium. Next, the image forming region on the recording medium on which the pretreatment solution has been ejected is exposed to light. Thus, sulfonic acid is generated in the image forming region from the photoacid generator contained in the pretreatment solution. Then, an image is formed by ejecting an ink onto the image forming region on the recording medium. At this point, an aggregation reaction is caused in the image forming region between the sulfonic acid generated from the pretreatment solution and a pigment contained in the ink. As a result, fixation of the pigment onto the recording medium is accelerated to improve image quality of the image. As improvement of the image quality, for example, an image density is increased, and feathering (ink bleed) and color bleed are inhibited. It is noted that color bleed refers to an image deterioration phenomenon occurring in a boundary (between dots) on which inks of different colors (dots) are adjacent to each other. In an image where the color bleed occurs, a pigment of one ink is mixed, in dots adjacent to each other, with the other ink to blur the image.

Besides, the pretreatment solution according to the present embodiment can inhibit ink nozzle clogging as compared with a known pretreatment solution (such as a pretreatment solution containing an acid component or a metal ion as an active ingredient). By the way, when a pretreatment solution is ejected in an inkjet recording apparatus, a part of the ejected pretreatment solution may be diffused in the form of a mist to adhere to a nozzle surface of a recording head in some cases. When the pretreatment solution thus adheres to the nozzle surface of the recording head, it is apprehended, in using the known pretreatment solution, that an ink nozzle may be clogged due to an aggregation reaction caused on the nozzle surface between the pretreatment solution and a pigment contained in an ink. On the contrary, the photoacid generator contained in the pretreatment solution of the present embodiment is a component that generates an acid component through light exposure, but does not cause an aggregation reaction with a pigment by itself. Therefore, the pretreatment solution of the present embodiment is difficult to clog the ink nozzle even if it adheres to the nozzle surface of the recording head. In this manner, since the pretreatment solution of the present embodiment contains the photoacid generator, the image quality of an image to be formed can be improved with ink nozzle clogging inhibited.

[Photoacid Generator]

The photoacid generator is a compound that generates sulfonic acid through light exposure. Examples of the photoacid generator include a triarylsulfonium salt derivative, a diaryliodonium salt derivative, a sulfonyl diazomethane derivative, a sulfonic acid ester derivative of N-hydroxyphthalimide, and compounds respectively represented by the following general formulas (I) and (II) (hereinafter sometimes referred to respectively as the photoacid generators (I) and (II)).

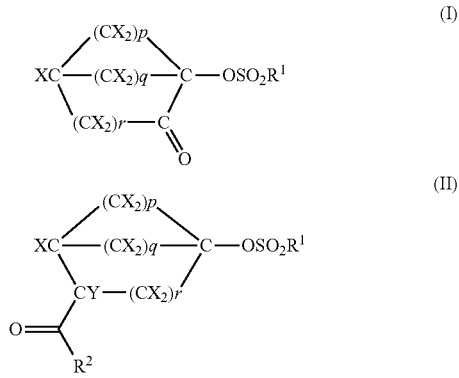

In the general formulas (I) and (II), $R^1$ represents an alkyl group optionally substituted with a first substituent, a cycloalkyl group optionally substituted with a second substituent, an aryl group optionally substituted with the second substituent, a heterocyclic group optionally substituted with the second substituent, a fluorine atom, a nitro group, or a cyano group. $R^2$ represents a hydrogen atom, an alkyl group optionally substituted with the first substituent, an alkenyl group optionally substituted with the first substituent, an alkynyl group optionally substituted with the first substituent, a cycloalkyl group optionally substituted with the second substituent, a cycloalkenyl group optionally substituted with the second substituent, a cycloalkynyl group optionally substituted with the second substituent, an aryl group optionally substituted with the second substituent, a heterocyclic group optionally substituted with the second substituent, an acylamide group, a sulfonylamide group, or a halogen atom. The first substituent is a fluorine atom or an aryl group. The second substituent is a fluorine atom, an alkyl group, a fluoroalkyl group, an alkoxy group, a carboxy group, an alkylcarbonyl group, or an alkylamino group. X represents a hydrogen atom or a methyl group. A plurality of Xs may be the same as or different from one another. When there is X bonding to a carbon atom in γ-position of a carbonyl group, at least one X bonding to a carbon atom in γ-position is a hydrogen atom. Y represents a hydrogen atom or a methyl group. p represents an integer of at least 1 and no greater than 3. q represents an integer of at least 0 and no greater than 3. r represents 1 or 2.

The photoacid generator is preferably the photoacid generator (I) or (II). The photoacid generators (I) and (II) generate sulfonic acid ($HOSO_2R^1$) through light exposure. Therefore, the acidity of the acid to be generated can be adjusted by changing the structure of $R^1$ in the photoacid generator (I) or (II). Since the photoacid generators (I) and (II) are nonionic compounds, these are excellent in compatibility with an organic solvent, and can be dissolved in a water-soluble organic solvent described later in an optional rate. Besides, a monovalent group represented by $OSO_2R^1$ in the photoacid generator (I) or (II) bonds to a carbon atom in a bridgehead position of a bridged ring hydrocarbon structure (hereinafter sometimes referred to as the carbon atom (α)). The carbon atom (α) is in the bridgehead position of the bridged ring hydrocarbon structure, and hence cannot be a target of a bimolecular nucleophilic substitution reaction ($SN_2$ reaction). Besides, the carbon atom (α) is in the bridgehead position of the bridged ring hydrocarbon structure, and hence becomes unstable due to molecular strain when in the form of a carbocation. Therefore, the carbon atom (α) cannot be or is very difficult to be a target of unimolecular nucleophilic substitution reaction ($SN_1$ reaction). In this manner, the photoacid generators (I) and (II) are comparatively stable against heat and a nucleophile unless exposed to light because the monovalent group represented by $OSO_2R^1$ bonds to the carbon atom (α). Therefore, when the photoacid generator (I) or (II) is used as the photoacid generator, storage stability of the pretreatment solution can be improved.

The alkyl group represented by $R^1$ is preferably an alkyl group having a carbon number of at least 1 and no greater than 5. The alkyl group represented by $R^1$ is optionally substituted with the first substituent as described above.

The first substituent in $R^1$ is preferably a fluorine atom or a phenyl group.

The cycloalkyl group represented by $R^1$ is preferably a cycloalkyl group having a carbon number of at least 5 and no greater than 10. The cycloalkyl group represented by $R^1$ is optionally substituted with the second substituent as described above.

The aryl group represented by $R^1$ is preferably an aryl group having a carbon number of at least 6 and no greater than 10. The aryl group represented by $R^1$ is optionally substituted by the second substituent as described above.

The heterocyclic group represented by $R^1$ is preferably a heterocyclic group having at least 5 and no greater than 10 ring members. The heterocyclic group represented by $R^1$ is optionally substituted with the second substituent as described above.

The second substituent in $R^1$ is preferably a fluorine atom, an alkyl group having a carbon number of at least 1 and no greater than 5, a fluoroalkyl group having a carbon number of at least 1 and no greater than 5, an alkoxy group having a carbon number of at least 1 and no greater than 5, a carboxy group, an alkylcarbonyl group having a carbon number of at least 2 and no greater than 5, or an alkylamino group having a carbon number of at least 1 and no greater than 5, and is more preferably a fluorine atom, a methyl group, a trifluoromethyl group, a pentafluoroethyl group, a methoxy group, a carboxy group, a methylcarbonyl group, or a dimethylamino group.

$R^1$ preferably represents an alkyl group having a carbon number of at least 1 and no greater than 5 and optionally substituted with the first substituent, more preferably represents an alkyl group having a carbon number of at least 1 and no greater than 5 or a fluoroalkyl group having a carbon number of at least 1 and no greater than 5, further preferably represents a perfluoroalkyl group having a carbon number of at least 1 and no greater than 5, and particularly preferably represents a trifluoromethyl group.

The alkyl group, the alkenyl group, and the alkynyl group represented by $R^2$ are respectively preferably an alkyl group having a carbon number of at least 1 and no greater than 5, an alkenyl group having a carbon number of at least 2 and no greater than 5, and an alkynyl group having a carbon number of at least 2 and no greater than 5. The alkyl group, the alkenyl group, and the alkynyl group represented by $R^2$ are optionally substituted with the first substituent as described above.

The first substituent in $R^2$ is preferably a fluorine atom or a phenyl group.

The cycloalkyl group, the cycloalkenyl group, and the cycloalkynyl group represented by $R^2$ are respectively preferably a cycloalkyl group having a carbon number of at least 5 and no greater than 10, a cycloalkenyl group having a carbon number of at least 5 and no greater than 10, and a cycloalkynyl group having a carbon number of at least 5 and no greater than 10. The cycloalkyl group, the cycloalkenyl group, and the cycloalkynyl group represented by $R^2$ are optionally substituted with the second substituent as described above.

The aryl group represented by $R^2$ is preferably an aryl group having a carbon number of at least 6 and no greater than 10, and more preferably a phenyl group. The aryl group represented by $R^2$ is optionally substituted with the second substituent as described above.

The acylamide group represented by $R^2$ is a group represented by $R^A$—(C=O)—NH—* (wherein $R^A$ represents an alkyl group or an aryl group; and * represents a binding site). The acylamide group represented by $R^2$ can be, for example, an acylamide group having a carbon number of at least 2 and no greater than 10. The acylamide group represented by $R^2$ is preferably an acetylamide group, a propionylamide group, an n-butyrylamide group, an isobutyrylamide group, a pivaloylamide group, or a benzoylamide group.

The sulfonylamide group represented by $R^2$ is a group represented by $R^B$—(SO$_2$)—NH—* (wherein $R^B$ represents an alkyl group or an aryl group; and * represents a binding site). The sulfonylamide group represented by $R^2$ can be a sulfonylamide group having a carbon number of at least 1 and no greater than 10. The sulfonylamide group represented by $R^2$ is preferably a mesylamide group, an n-propanesulfonylamide group, an n-butanesulfonylamide group, an i-butanesulfonylamide group, a t-butanesulfonylamide group, or a benzenesulfonylamide group.

The halogen atom represented by $R^2$ is preferably a fluorine atom.

$R^2$ preferably represents an alkyl group having a carbon number of at least 1 and no greater than 5 and optionally substituted with the first substituent, or an aryl group having a carbon number of at least 6 and no greater than 14 and optionally substituted with the second substituent, more preferably represents an alkyl group having a carbon number of at least 1 and no greater than 5, or an aryl group having a carbon number of at least 6 and no greater than 10, and further preferably represents a methyl group or a phenyl group.

Y preferably represents a hydrogen atom.

p preferably represents 2. q preferably represents 1. r preferably represents 1.

The photoacid generator (I) or (II) is preferably a compound represented by the following chemical formula (II-1) or (II-2) (hereinafter sometimes referred to as the photoacid generator (II-1) or (II-2).

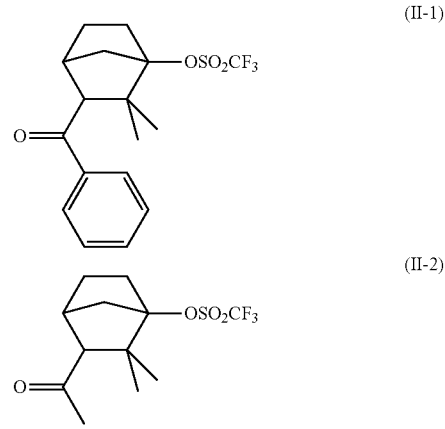

(II-1)

(II-2)

The photoacid generator (I) or (II) can be synthesized, for example, through Jones oxidation of a hydroxy compound represented by the following general formula (I') or (II').

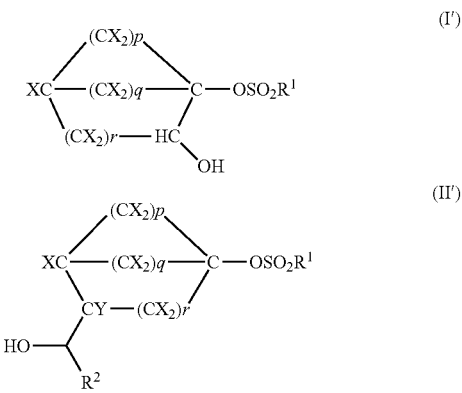

(I')

(II')

In the general formulas (I') and (II'), $R^1$, $R^2$, X, Y, p, q, and r have the same meanings as in the general formulas (I) and (II).

An example of the triarylsulfonium salt derivative usable as the photoacid generator includes a compound represented by the following general formula (S-1), (S-2), or (S-3). An example of the diaryliodonium salt derivative usable as the photoacid generator includes a compound represented by the following chemical formula (I-1) or (1-2), or general formula (I-3). An example of the sulfonyl diazomethane derivative usable as the photoacid generator includes a compound represented by the following chemical formula (A-1). An example of the sulfonic acid ester derivative of N-hydroxyphthalimide usable as the photoacid generator includes a compound represented by the following chemical formula (A-2).

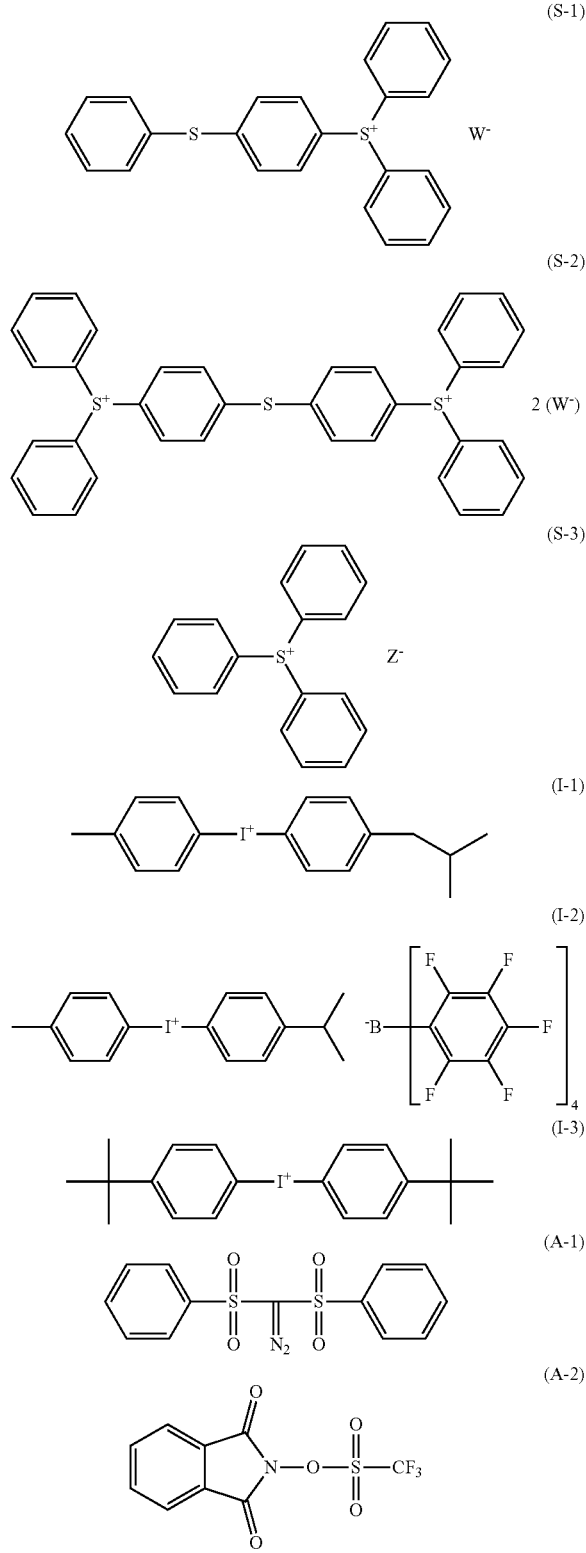

In the general formulas (S-1) and (S-2), W⁻ represents $PF_6^-$ or $SbF_6^-$. In the general formulas (S-3) and (I-3), Z⁻ represents $CF_3SO_3^-$ or $C_4F_9SO_3^-$.

A content rate of the photoacid generator in the pretreatment solution is preferably at least 0.1% by mass and no greater than 5.0% by mass, and more preferably at least 0.2% by mass and no greater than 2.0% by mass.

[Water]

Water works as a major solvent of the pretreatment solution. Since the pretreatment solution contains water as the major solvent, environmental load can be reduced. When the pretreatment solution contains water, a content rate thereof is preferably at least 60% by mass and no greater than 95% by mass, and more preferably at least 80% by mass and no greater than 90% by mass.

[Water-Soluble Organic Solvent]

The water-soluble organic solvent improves solubility of the photoacid generator in the pretreatment solution. The water-soluble organic solvent stabilizes viscosity of the pretreatment solution by inhibiting volatilization of a liquid component of the pretreatment solution. Examples of the water-soluble organic solvent include glycol compounds such as ethylene glycol, propylene glycol, diethylene glycol, triethylene glycol, and tetraethylene glycol; glycerin; ether compounds of polyhydric alcohols such as diethylene glycol diethyl ether, diethylene glycol monobutyl ether, ethylene glycol monomethyl ether, ethylene glycol monobutyl ether, methyl carbitol, ethyl carbitol, butyl carbitol, ethyl carbitol acetate, diethyl carbitol, triethylene glycol monomethyl ether, triethylene glycol monoethyl ether, and propylene glycol monomethyl ether; an acetate compound; thiodiglycol; nitrogen-containing compounds such as a lactam compound (for example, 2-pyrrolidone or N-methyl-2-pyrrolidone), 1,3-dimethylimidazolidine, formamide, and dimethylformamide; and dimethyl sulfoxide.

The pretreatment solution contains, as the water-soluble organic solvent, preferably at least one of glycerin and a lactam compound, more preferably glycerin and a lactam compound, and further preferably glycerin and 2-pyrrolidone.

When the pretreatment solution contains the water-soluble organic solvent, a total content rate thereof is preferably at least 2% by mass and no greater than 40% by mass, and more preferably at least 7% by mass and no greater than 25% by mass.

When the pretreatment solution contains glycerin, a content rate thereof is preferably at least 1% by mass and no greater than 25% by mass, and more preferably at least 5% by mass and no greater than 15% by mass.

When the pretreatment solution contains a lactam compound, a content rate thereof is preferably at least 1% by mass and no greater than 15% by mass, and more preferably at least 2% by mass and no greater than 10% by mass.

The pretreatment solution contains, as a solvent, preferably water, glycerin, and a lactam compound alone. A total content rate of water, glycerin and a lactam compound in the solvent of the pretreatment solution is preferably at least 90% by mass, and more preferably at least 99% by mass.

[Surfactant]

The surfactant improves wettability of the pretreatment solution on a recording medium. The surfactant is preferably a nonionic surfactant, and more preferably an acetylene glycol-based surfactant (such as "OLFINE (registered Japanese trademark) E1010", that is, an ethylene oxide adduct of acetylene diol, manufactured by Nissin Chemical Industry Co., Ltd.).

When the pretreatment solution contains the surfactant, a content rate thereof is preferably at least 0.01% by mass and no greater than 2.00% by mass, and more preferably at least 0.05% by mass and no greater than 0.50% by mass.

[Preparation Method for Pretreatment Solution]

The pretreatment solution can be prepared by adding, to a solvent, a photoacid generator, and an optional component such as a surfactant added if necessary.

Second Embodiment: Inkjet Recording Apparatus

An inkjet recording apparatus according to a second embodiment of the present disclosure is an inkjet recording apparatus for forming an image in an image forming region on a recording medium, and includes a pretreating section that ejects the pretreatment solution of the first embodiment onto the image forming region on the recording medium; an exposing section that exposes the image forming region on which the pretreatment solution has been ejected to light; and a recording head that forms an image by ejecting an ink onto the exposed image forming region on the recording medium. The inkjet recording apparatus according to the second embodiment uses the pretreatment solution according to the first embodiment, and hence the image quality of an image to be formed can be improved with ink nozzle clogging inhibited.

An example of the inkjet recording apparatus of the second embodiment will now be described with reference to the accompanying drawing. FIGURE is a side view illustrating a principal part of an inkjet recording apparatus 1. The inkjet recording apparatus 1 includes at least a pretreating section 2 that ejects the pretreatment solution onto an image forming region on a recording medium (not shown), an exposing section 3 that exposes the image forming region on the recording medium on which the pretreatment solution has been ejected to light, four recording heads 4 (specifically, a first recording head 4a, a second recording head 4b, a third recording head 4c, and a fourth recording head 4d) that forms an image by ejecting inks onto the exposed image forming region on the recording medium, and a conveyance belt 5 that conveys the recording medium. The four recording heads 4 respectively eject different inks (for example, a yellow ink, a magenta ink, a cyan ink, and a black ink). The inkjet recording apparatus 1 forms a full-color image on the recording medium based on, for example, image data and printing conditions (specifically, for example, whether or not double-sided printing is performed) received from an external computer.

The conveyance belt 5 is, for example, a part of an endless belt, and conveys the recording medium in one direction (in the rightward direction in the drawing). The pretreating section 2, the exposing section 3, and the recording heads 4 (specifically, the first recording head 4a, the second recording head 4b, the third recording head 4c, and the fourth recording head 4d) are disposed above the conveyance belt 5 in the stated order along the conveyance direction of the recording medium. In the inkjet recording apparatus 1, while the recording medium is being conveyed by the conveyance belt 5, the ejection of the pretreatment solution onto the image forming region, the light exposure, and the ink ejection are performed respectively when the image forming region on the recording medium is conveyed to portions directly below the pretreating section 2, the exposing section 3, and the recording heads 4. The inkjet recording apparatus 1 has been described so far with reference to the accompanying drawing.

It is noted, however, that the one illustrated in the drawing is merely an example of the inkjet recording apparatus according to the second embodiment. Specifically, the number of recording heads included in the inkjet recording apparatus of the second embodiment may be merely one (namely, the inkjet recording apparatus may be for forming a monochrome image), or may be two, three, five or more. Besides, the inkjet recording apparatus of the second embodiment need not include the conveyance belt. In this case, the inkjet recording apparatus may include a movable pretreating section, a movable exposing section, and a movable recording head. In other words, the inkjet recording apparatus may perform the pretreatment of the image forming region, the light exposure, and the ink ejection with the pretreating section, the exposing section, and the recording head successively moved to a portion above the image forming region on the recording medium instead of conveying the recording medium. Furthermore, the inkjet recording apparatus may further include an additional member in addition to the pretreating section, the exposing section, the recording head, and the conveyance belt. Examples of the additional member included in the inkjet recording apparatus include a supplying section that supplies the recording medium to the conveyance belt, a post-treating section that performs a post-treatment (such as a drying treatment) on the recording medium having an image formed thereon, a cleaning section that cleans the recording head after the ink ejection, an electronic controller (such as a CPU or memory), an input section (such as a keyboard, a mouse, or a touch panel), and a communicating section. The recording medium, the pretreating section, the exposing section, and the recording head will now be described in detail.

[Recording Medium]

The recording medium is not limited in the material, the shape, and the thickness as long as it is a sheet-shaped member. Examples of the recording medium include printing paper (such as coated paper or gravure paper), cloth (such as a polyester fabric), and a resin film (such as a polyester film). The inkjet recording apparatus of the second embodiment performs the pretreatment using the pretreatment solution of the first embodiment, and therefore, a high quality image can be formed even on a recording medium having low liquid absorption such as a resin film or coated paper, or a fabric having high water repellency such as a polyester fabric.

[Pretreating Section]

The pretreating section ejects the pretreatment solution onto the image forming region on the recording medium. A method for ejecting the pretreatment solution is not especially limited, and may be, for example, a piezo method, a thermal inkjet method, and a spray method.

An ejection amount of the pretreatment solution can be appropriately changed in accordance with the recording medium, and can be, for example, at least 1 nL and no greater than 10 nL per $mm^2$ of the image forming region on the recording medium.

[Exposing Section]

The exposing section exposes to light the image forming region on the recording medium on which the pretreatment solution has been ejected. Thus, an acid component is generated from the photoacid generator contained in the pretreatment solution in the image forming region on the recording medium. As exposing light, for example, exposing light including light having a wavelength shorter than 400 nm can be used. The wavelength of the exposing light is preferably at least 300 nm and no grater than 400 nm, and more preferably at least 350 nm and no greater than 400 nm. The exposing light can be, for example, a resonance line of a high pressure mercury lamp (313 nm and 254 nm), KrF excimer laser light (248 nm), or ArF excimer laser light (193 nm). An exposure dose can be, for example, at least 1 $mJ/cm^2$ and no greater than 100 $mJ/cm^2$.

[Recording Head]

The recording head ejects an ink onto the exposed image forming region on the recorded medium to form an image. A pigment contained in the ejected ink causes an aggregation reaction with the acid component present in the image forming region. Thus, fixation of the pigment contained in the ink onto the image forming region is accelerated to form a high quality image. The recording head is not especially limited, and can be any recording head (for example, a recording head of a line head type or a recording head of a serial head type) included in a general inkjet recording apparatus.

(Ink)

As the ink ejected from the recording head, any ink (for example, a water-based ink) used in a general inkjet recording apparatus can be used. A water-based ink contains, for example, an aqueous medium and pigment particles. The pigment particles are present in the aqueous medium to be dispersed from one another. Each of the pigment particles may be a particle containing a pigment core alone, or may be a particle containing a pigment core and a coating resin coating at least a part of the surface of the pigment core. The water-based ink may further contain at least one of a surfactant and a water-soluble organic solvent.

(Pigment Core)

The pigment core contains a pigment. Examples of the pigment include a yellow pigment, an orange pigment, a red pigment, a blue pigment, a violet pigment, and a black pigment. Examples of the yellow pigment include C.I. Pigment Yellow 74, 93, 95, 109, 110, 120, 128, 138, 139, 151, 154, 155, 173, 180, 185, and 193. Examples of the orange pigment include C.I. Pigment Orange 34, 36, 43, 61, 63, and 71. Examples of the red pigment include C.I. Pigment Red 122 and 202. Examples of the blue pigment include C.I. Pigment Blue 15 and 15:3. Examples of the violet pigment includes C.I. Pigment Violet 19, 23, and 33. An example of the black pigment includes C.I. Pigment Black 7.

When the water-based ink contains the pigment core, a content rate thereof is preferably at least 4% by mass and no greater than 8% by mass. When the content of the pigment core is at least 4% by mass, an image having a desired image density can be easily formed. On the other hand, when the content of the pigment core is no greater than 8% by mass, permeability of the water-based ink into the recording medium can be easily obtained. Besides, when the content of the pigment core is no greater than 8% by mass, flowability of the pigment cores in the water-based ink can be easily obtained, resulting in easily forming an image having a desired image density.

A volume median diameter ($D_{50}$) of the pigment cores is, from the viewpoint of color density, hue and stability of the water-based ink, preferably at least 30 nm and no greater than 200 nm, and more preferably at least 70 nm and no greater than 130 nm.

The surfactant improves wettability of the water-based ink on the recording medium. The type and the content of the surfactant used in the water-based ink can be set similarly to the type and the content of the surfactant exemplified with respect to the pretreatment solution above.

The water-soluble organic solvent inhibits volatilization of a liquid component to stabilize viscosity of the water-based ink. The type and the content of the water-soluble organic solvent used in the water-based ink can be set similarly to the type and the content of the water-soluble organic solvent exemplified with respect to the pretreatment solution above.

The pretreatment solution and the water-based ink preferably contain the same type of the water-soluble organic solvent in the same content rate. Besides, the pretreatment solution and the water-based ink preferably contains the same type of the surfactant in the same content rate. When the compositions of the pretreatment solution and the water-based ink are thus close to each other, the pretreatment solution and the water-based ink having been ejected onto the recording medium can be easily mixed with each other, resulting in accelerating the aggregation reaction between the acid component generated from the photoacid generator contained in the pretreatment solution and the pigment contained in the water-based ink.

Third Embodiment: Image Forming Method

An image forming method according to a third embodiment of the present disclosure is a method for forming an image in an image forming region on a recording medium, and includes ejecting the pretreatment solution according to the first embodiment onto the image forming region on the recording medium (hereinafter sometimes referred to as the pretreatment solution ejecting step); exposing, to light, the image forming region on the recording medium on which the pretreatment solution has been ejected (hereinafter sometimes referred to as the exposing step); and forming an image by ejecting an ink onto the exposed image forming region on the recording medium (hereinafter sometimes referred to as the ink ejecting step). In the image forming method according to the third embodiment, the pretreatment solution according to the first embodiment is used, and hence quality of an image to be formed can be improved with ink nozzle clogging inhibited.

In the image forming method according to the third embodiment, for example, the inkjet recording apparatus according to the second embodiment can be used. The recording medium and the ink used in the image forming method of the third embodiment can be similar to the recording medium and the ink used in the inkjet recording apparatus according to the second embodiment. The respective steps will now be described.

[Pretreatment Solution Ejecting Step]

In this step, the pretreatment solution according to the first embodiment is ejected onto the image forming region on the recording medium. A method for ejecting the pretreatment solution is not especially limited, and can be, for example, a method in which the pretreating section described in the second embodiment is used for the ejection.

[Exposing Step]

In this step, the image forming region on the recording medium onto which the pretreatment solution has been ejected is exposed to light. Thus, an acid component is generated from the photoacid generator contained in the pretreatment solution. An exposing method is not especially limited, and can be, for example, a method in which the exposing section described in the second embodiment is used for the light exposure.

[Ink Ejecting Step]

In this step, an image is formed by ejecting the ink onto the exposed image forming region on the recording medium. A method for ejecting the ink is not especially limited, and can be, for example, a method in which the recording head described in the second embodiment is used for the ejection.

The image forming method according to the third embodiment may further include an additional step in addition to the pretreatment solution ejecting step, the exposing step, and the ink ejecting step. Examples of the additional step include a post-treatment step of performing a post-treatment (such as a drying treatment) on the recording medium on which the image has been formed, and a cleaning step of cleaning the recording head after the ink ejection.

Examples

The present disclosure will now be more specifically described with reference to examples. It is noted that the present disclosure is not limited to the scope of these examples at all.

[Preparation of Photoacid Generator]

The photoacid generators (II-1) and (II-2) described in the first embodiment were prepared by the following methods.

(Photoacid Generator (II-1))

An eggplant-shaped flask was charged with 30 mL of an acetone solution in which 0.272 g (0.719 mmol) of 2,2-dimethyl-3-phenylhydroxymethyl[2.2.1]bicycloheptan-1-triflate was dissolved. Jones reagent (a sulfuric acid solution of chromic anhydride (CrO₃) (0.1 mol/L)) was gradually added in a dropwise manner to the acetone solution under ice cooling. The dropwise addition amount of the Jones reagent was 15 mL in total. After the dropwise addition, chromium (III) precipitated in the resultant reaction solution was removed by filtering. Then, acetone was distilled off, using a rotary evaporator, from the reaction solution after the filtering. The thus obtained solution was put into 30 mL of a saturated saline solution. A product contained in the resultant mixture (aqueous layer) was subjected to solvent extraction with diethyl ether (organic layer). Specifically, 30 mL of diethyl ether was put into the mixture to extract the organic layer. After the extraction, the organic layer containing the product was dried by putting 0.5 g of anhydrous magnesium sulfate thereinto. After the drying, diethyl ether was distilled off from the organic layer using a rotary evaporator. The resultant solution obtained after distilling was subjected to isolation and purification by silica gel column chromatography (eluent: benzene) to obtain 3-benzoyl-2,2-dimethyl[2.2.1]bicycloheptan-1-triflate (photoacid generator (II-1)). The yield amount of the photoacid generator (II-1) was 0.181 g, and the yield was 67%.

(Photoacid Generator (II-2))

An eggplant-shaped flask was charged with 30 mL of an acetone solution in which 0.315 g (0.996 mmol) of 2,2-dimethyl-3-(2-hydroxy)methyl[2.2.1]bicycloheptan-1-triflate was dissolved. Jones reagent (a sulfuric acid solution of chromic anhydride (CrO₃) (0.1 mol/L)) was gradually added in a dropwise manner to the acetone solution under ice cooling. The dropwise addition amount of the Jones reagent was 18 mL in total. After the dropwise addition, chromium (III) precipitated in the resultant reaction solution was removed by filtering. Then, acetone was distilled off, using a rotary evaporator, from the reaction solution after the filtering. The thus obtained solution was put into 30 mL of a saturated saline solution. A product contained in the resultant mixture (aqueous layer) was subjected to solvent extraction with diethyl ether (organic layer). Specifically, 30 mL of diethyl ether was put into the mixture to extract the organic layer. After the extraction, the organic layer containing the product was dried by putting 0.5 g of anhydrous magnesium sulfate thereinto. After the drying, diethyl ether was distilled off from the organic layer using a rotary evaporator. The resultant solution obtained after distilling was subjected to isolation and purification by the silica gel column chromatography (eluent: benzene) to obtain 3-acetyl-2,2-dimethyl[2.2.1]bicycloheptan-1-triflate (photoacid generator (II-2)). The yield amount of the photoacid generator (II-2) was 0.219 g, and the yield was 70%.

As an ionic photoacid generator, "TPS-TF" manufactured by Toyo Gosei Co., Ltd. was prepared. This compound was a compound represented by the following chemical formula (s-1). Besides, as an acid component to be used in a comparative example, "Magnesium Chloride Hexahydrate" manufactured by FUJIFILM Wako Pure Chemical Corporation was prepared.

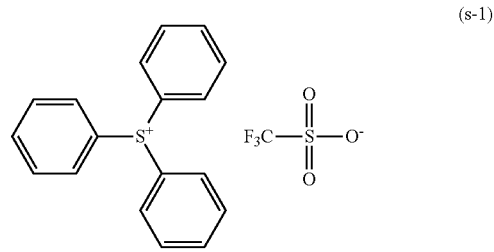 [SMILES: c1ccc([S+](c2ccccc2)c2ccccc2)cc1 ; O=S(=O)([O-])C(F)(F)F]

(s-1)

[Preparation of Pretreatment Solution]

0.5 g of the photoacid generator (II-1) used as the photoacid generator, 10.0 g of glycerin and 5.0 g of 2-pyrrolidone used as the water-soluble organic solvents, and 0.1 g of "OLFINE (registered Japanese trademark) E1010" manufactured by Nissin Chemical Industry Co., Ltd. used as the surfactant were added to ion-exchanged water to prepare a mixture of a total amount of 100.0 g. Thus, a pretreatment solution (A-1) was obtained.

Pretreatment solutions (A-2) and (A-3) and a pretreatment solution (B-1) were prepared through an operation performed in the same manner as in the preparation of the pretreatment solution (A-1) except for making the following changes. Specifically, in the preparation of the pretreatment solutions (A-2) and (A-3), the type and the use amount of the photoacid generator were changed as shown in Table 1 below. Besides, the acid component was used instead of the photoacid generator for the pretreatment solution (B-1).

The type and the use amount of the photoacid generator or the acid component used for each pretreatment solution are shown in Table 1 below. In Table 1, "II-1" and "II-2" respectively indicate the photoacid generators (II-1) and (II-2); and "-" indicates that the corresponding component was not used.

TABLE 1

| Pretreatment Solution | Photoacid Generator | | Acid Component | |
|---|---|---|---|---|
| | Type | Amount [g] | Type | Amount [g] |
| A-1 | II-1 (nonionic) | 0.5 | — | — |
| A-2 | II-2 (nonionic) | 0.5 | — | — |
| A-3 | TPS-TF (ionic) | 0.5 | — | — |
| B-1 | — | — | Magnesium Chloride Hexahydrate | 0.02 |

[Preparation of Black Ink]

90 g of carbon black ("#990" manufactured by Mitsubishi Chemical Corporation, nitrogen adsorption specific surface area: 250 m²/g, DBP oil absorption: 112 mL/100 g) was added to 3000 mL of a 2.5 normal sodium persulfate solution. An oxidation treatment was performed by causing a reaction by stirring the resultant reaction solution at a temperature of 60° C. and a speed of 300 rpm for 10 hours.

Thereafter, the resultant reaction solution was filtered to filter off the carbon black having been subjected to the oxidation treatment. The thus filtered carbon black was put into 100 mL of a sodium hydroxide solution to be neutralized, and thereafter, the resultant was subjected to ultrafiltration. The thus obtained neutralized carbon black was washed with water and then dried, and thereafter, was dispersed in pure water to obtain a solid content of 30% by mass, and the resultant was sufficiently stirred to obtain a black pigment dispersion. A volume median diameter ($D_{50}$) of pigment dispersing elements (pigment cores) in this black pigment dispersion was 103 nm.

20.0 g of the black pigment dispersion (6.0 g in terms of solid content), 10.0 g of glycerin and 5.0 g of 2-pyrrolidone used as the water-soluble organic solvents, and 0.1 g of "OLFINE (registered Japanese trademark) E1010" manufactured by Nissin Chemical Industry Co., Ltd. used as the surfactant were added to ion-exchanged water to prepare a mixture of a total amount of 100.0 g. Thus, a black ink was obtained.

[Preparation of Yellow Ink]

20.0 g of pigment dispersing elements "TB-416 Yellow (manufactured by Dainichiseika Color & Chemicals Mfg. Co., Ltd.) (2.0 g in terms of solid content), 10.0 g of glycerin and 5.0 g of 2-pyrrolidone used as the water-soluble organic solvents, and 0.1 g of "OLFINE (registered Japanese trademark) E1010" manufactured by Nissin Chemical Industry Co., Ltd. used as the surfactant were added to ion-exchanged water to prepare a mixture of a total amount of 100.0 g. Thus, a yellow ink was obtained.

<Evaluation>

The pretreatment solutions (A-1) to (A-3) and (B-1) were evaluated for storage stability, ink nozzle clogging, and image quality of an image formed therewith (Examples 1 to 3 and Comparative Example 1). Besides, an image was formed without using any pretreatment solution to evaluate the ink nozzle clogging and the image quality of the formed image (Comparative Example 2). The evaluation was performed under environment of a temperature of 20° C. and a humidity of 30% RH. The evaluation results thus obtained are shown in Table 2 below.

(Evaluation Apparatus)

As an evaluation apparatus used for the image formation, a modified apparatus of an inkjet recording apparatus (an experimental apparatus manufactured by KYOCERA Document Solutions Inc.) including a conveyance unit (belt conveyor) and four recording heads (all of a line head type) was used. Each recording head of this experimental apparatus was a piezo head with resolution of 600 dpi (=150 dpi×4 rows), having 2400 (=600×4 rows) nozzles, a droplet amount of 11 pL, and a drive frequency of 20 kHz. The four recording heads of the experimental apparatus were disposed to have their lengthwise direction perpendicularly to a paper conveyance direction. A distance between adjacent ones of the four recording heads was 50 mm. In the modification, an exposing section (UV irradiation apparatus, "UniJet (registered Japanese trademark) A360" manufactured by Ushio Inc.) was additionally provided on the upstream side in the conveyance direction from the four recording heads, and a pretreating section was additionally provided on the further upstream side in the conveyance direction from the exposing section. Light exposure conditions were set to a wavelength of 385 nm and an exposure dose of 60 mJ/cm$^2$. The pretreating section was set by using a piezo head of the same type as a recording head to eject the pretreatment solution. The ejection amount of the pretreatment solution was set to 3.4 nL per mm$^2$ of an image forming region on a recording medium.

The black ink and the yellow ink described above were set to be ejected respectively from the two recording heads out of the four recording heads. It is noted that the other two recording heads were not used.

[Nozzle Clogging]

An image of a coverage rate of 100% was printed continuously on 10000 sheets of A4 recording paper using the above-described evaluation apparatus. Thereafter, the number of miss-ejecting pins of the evaluation apparatus was counted, and nozzle clogging level was defined as follows.

A (good): The number of miss-ejecting pins was no greater than 5.

B (poor): The number of miss-ejecting pins was over 5.

[Storage Stability]

100 g of each of the pretreatment solutions was measured for pH, and then stored at 60° C. for 1 month, and thereafter, measured for pH again. Based on the measurement results of pH, the storage stability was obtained in accordance with the following expression.

Storage stability=pH before storage–pH after storage

A (good): An absolute value of the storage stability (pH change) was within 0.3.

B (poor): An absolute value of the storage stability (pH change) was over 0.3.

[Image Evaluation]

The above-described evaluation apparatus was used to form an image on each of the following recording media to evaluate the image density, the feathering, and the color bleed.

(Recording Media)

The following recording media were prepared for the evaluation.

Coated paper A: "POD GLOSS COAT (business coat gloss)" manufactured by Oji Paper Co., Ltd., basis weight: 100 g/m$^2$ Coated paper B: "OK TOPCOAT+" manufactured by Oji Paper Co., Ltd., basis weight: 104.7 g/m$^2$ Gravure paper: "SPACE DX" manufactured by Oji Paper Co., Ltd., basis weight: 56.5 g/m$^2$ Coated paper C: "SUPERFINE PAPER (matte coated paper for inkjet recording)" manufactured by Seiko Epson Corporation, basis weight: 102 g/m$^2$ Transparent polyester film (PEs film): "LUMIRROR (registered Japanese trademark) U10" manufactured by Toray Industries, Inc., thickness: 100 μm Polyester fabric (PEs fabric): "POLYESTER TAFFETA" manufactured by Shikisensha Co., Ltd., basis weight: 71.8 g/m$^2$ (Image Density)

Each of the recording media was pretreated with each of the pretreatment solutions having been subjected to the storage at 60° C. for 1 month or each of the pretreatment solutions not subjected to the storage, and then, a black solid image of 2 cm×2 cm was formed using the evaluation apparatus. The resolution was set to 600 dpi. An image density of a black solid portion thus formed was measured using "Reflective Spectrophotometric Color Densitometer" manufactured by X-Rite. An image density having a larger measured value means that the image has a higher density. The image density was evaluated to be good (A) or poor (B) in accordance with the following criteria.

When the recording medium was the coated paper A, the coated paper B, the gravure paper, or the coated paper C, the following criteria were employed. Based on two image densities obtained by using the pretreatment solution before the storage and after the storage, when "both the image densities were at least 1.3, and a difference in the image density was smaller than 0.1", it was evaluated as good (A), and when "at least one of the image densities was lower than 1.3, or a difference in the image density was at least 0.1", it was evaluated as poor (B).

When the recording medium was the PEs film, the following criteria were employed. Based on the two image densities obtained by using the pretreatment solution before the storage and after the storage, when "both the image densities were at least 2.0, and a difference in the image density was smaller than 0.1", it was evaluated as good (A), and when "at least one of the image densities was lower than 2.0, or a difference in the image density was at least 0.1", it was evaluated as poor (B).

When the recording medium was the PEs fabric, the following criteria were employed. Based on the two image densities obtained by using the pretreatment solution before the storage and after the storage, when "both the image densities were at least 2.0, and a difference in the image density was smaller than 0.1", it was evaluated as good (A), and when "at least one of the image densities was lower than 2.0, or a difference in the image density was at least 0.1", it was evaluated as poor (B).

(Feathering)

Each of the recording media was pretreated with each of the pretreatment solutions having been subjected to the storage at 60° C. for 1 month, or each of the pretreatment solutions not subjected to the storage, and then, a black thin line having a width of 1 mm was formed using the evaluation apparatus and visually observed. The resolution was set to 600 dpi. The feathering was evaluated as good (A) when ink bleed (feathering) was not caused around the black thin line in using both the pretreatment solution before the storage and the pretreatment solution after the storage, and was evaluated as poor (B) when ink bleed was caused in using the pretreatment solution after the storage.

(Color Bleed)

Each of the recording media was pretreated with each of the pretreatment solutions having been subjected to the storage at 60° C. for 1 month, or each of the pretreatment solutions not subjected to the storage, and then, a black solid image of 4 cm×4 cm and a yellow solid image of 4 cm×4 cm were formed to be adjacent to each other using the evaluation apparatus, and a boundary between these images was visually observed. The resolution was set to 600 dpi. The color bleed was evaluated as good (A) when color mixture was not caused on the boundary between the black solid image and the yellow solid image in using both the pretreatment solution before the storage and the pretreatment solution after the storage, and was evaluated as poor (B) when color mixture was caused in using the pretreatment solution after the storage.

In Table 2 below, "-" indicates that the corresponding evaluation was not performed.

TABLE 2

| | Pretreatment Solution | Recording Medium | Image Density Measured Value (before storage/ after storage) | Evaluation | Feathering | Color Bleed | Nozzle Clogging | Storage Stability |
|---|---|---|---|---|---|---|---|---|
| Example 1 | A-1 | Coated Paper A | 1.5/1.5 | A | A | A | A | A |
| | | Coated Paper B | 1.4/1.4 | A | A | A | | |
| | | Gravure Paper | 1.8/1.8 | A | A | A | | |
| | | Coated Paper C | 1.8/1.8 | A | A | A | | |
| | | PEs Film | 2.1/2.1 | A | A | A | | |
| | | PEs Fabric | 2.5/2.5 | A | A | A | | |
| Example 2 | A-2 | Coated Paper A | 1.4/1.4 | A | A | A | A | A |
| | | Coated Paper B | 1.3/1.3 | A | A | A | | |
| | | Gravure Paper | 1.7/1.7 | A | A | A | | |
| | | Coated Paper C | 1.7/1.7 | A | A | A | | |
| | | PEs Film | 2.0/2.0 | A | A | A | | |
| | | PEs Fabric | 2.4/2.4 | A | A | A | | |
| Example 3 | A-3 | Coated Paper A | 1.5/1.5 | A | A | A | A | B |
| | | Coated Paper B | 1.5/1.5 | A | A | A | | |
| | | Gravure Paper | 1.7/1.7 | A | A | A | | |
| | | Coated Paper C | 1.8/1.8 | A | A | A | | |
| | | PEs Film | 2.0/2.0 | A | A | A | | |
| | | PEs Fabric | 2.4/2.4 | A | A | A | | |
| Comparative Example 1 | B-1 | Coated Paper A | 1.1/1.1 | B | B | B | B | A |
| | | Coated Paper B | 1.1/1.1 | B | B | B | | |
| | | Gravure Paper | 1.1/1.1 | B | B | B | | |

TABLE 2-continued

| | | Image Evaluation | | | | | | |
| | | Image Density | | | | | | |
| Pretreatment Solution | Recording Medium | Measured Value (before storage/after storage) | Evaluation | Feathering | Color Bleed | Nozzle Clogging | Storage Stability |
|---|---|---|---|---|---|---|---|
| | Coated Paper C | 1.2/1.2 | B | B | B | | |
| | PEs Film | 1.7/1.7 | B | B | B | | |
| | PEs Fabric | 1.7/1.7 | B | B | B | | |
| Comparative Example 2 | Coated Paper A | 1.2/— | B | B | B | A | — |
| | Coated Paper B | 1.2/— | B | B | B | | |
| | Gravure Paper | 1.2/— | B | B | B | | |
| | Coated Paper C | 1.3/— | B | B | B | | |
| | PEs Film | 1.8/— | B | B | B | | |
| | PEs Fabric | 1.8/— | B | B | B | | |

The pretreatment solutions (A-1) to (A-3) used in Examples 1 to 3 contained the photoacid generator that generates sulfonic acid through light exposure. As a result, as shown in Table 2, a high quality image could be formed with the ink nozzle clogging inhibited in Examples 1 to 3.

On the other hand, the pretreatment solution (B-1) used in Comparative Example 1 did not contain the photoacid generator that generates sulfonic acid through light exposure. Specifically, the pretreatment solution (B-1) did not contain a photoacid generator but contained an acid component instead. Therefore, as shown in Table 2, a high quality image could not be formed, and in addition, the ink nozzle clogging was caused in Comparative Example 1. This is probably because the acid component used in the pretreatment solution of Comparative Example 1 was insufficient in the acidity and the use amount, and hence the quality of an image to be formed could not be increased. Besides, in Comparative Example 1, a part of the ejected pretreatment solution (B-1) was diffused in the form of a mist to adhere to a nozzle surface of the recording head, and hence the aggregation reaction between the acid component and the pigment was probably caused on the nozzle surface. Incidentally, if an acid component having higher acidity was used, or the use amount of the acid component was increased in Comparative Example 1, the quality of an image to be formed could be improved, but the ink nozzle clogging was probably more easily caused.

Furthermore, in Comparative Example 2, the pretreatment solution was not used. Therefore, an image of sufficiently high quality could not be formed in Comparative Example 2.

Accordingly, it is determined that the pretreatment solution, the inkjet recording apparatus, and the image forming method according to the present disclosure can improve quality of an image to be formed with ink nozzle clogging inhibited.

Incidentally, the pretreatment solutions (A-1) and (A-2) used in Examples 1 and 2 were more excellent in the storage stability than the pretreatment solution (A-3) used in Example 3. This is probably because the pretreatment solutions (A-1) and (A-2) are nonionic compounds represented by the general formulas (I) and (II) described in the first embodiment, and hence are stable against heat and a nucleophile as described above.

Accordingly, the pretreatment solution, the inkjet recording apparatus, and the image forming method according to the present disclosure can also improve the storage stability when a compound represented by the general formula (I) or (II) is used as the photoacid generator contained in the pretreatment solution.

What is claimed is:
1. A pretreatment solution for inkjet recording comprising a photoacid generator that generates sulfonic acid through light exposure,
wherein the photoacid generator is a compound represented by general formula (I) or (II) shown below,

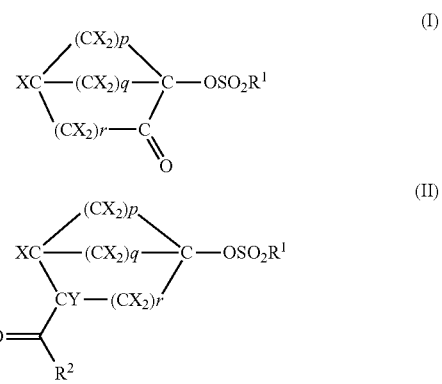

where in general formulae (I) and (II),
R$^1$ represents an alkyl group optionally substituted with a first substituent, a cycloalkyl group optionally substituted with a second substituent, an aryl group optionally substituted with the second substituent, a heterocyclic group optionally substituted with the second substituent, a fluorine atom, a nitro group, or a cyano group,
R$^2$ represents a hydrogen atom, an alkyl group optionally substituted with the first substituent, an alkenyl group optionally substituted with the first substituent, an alkynyl group optionally substituted with the first substituent, a cycloalkyl group optionally substituted with the second substituent, a cycloalkenyl group optionally substituted with the second substituent, a cycloalkynyl group optionally substituted with the second substituent, an aryl group optionally substituted with the second substituent, a heterocyclic group optionally substituted with the second substituent, an acylamide group, a sulfonylamide group, or a halogen atom, the first substituent is a fluorine atom or an aryl group, the second substituent is a fluorine atom, an alkyl group, a fluoroalkyl group, an alkoxy group, a carboxy group, an alkylcarbonyl group, or an alkylamino group, X represents a hydrogen atom or a methyl group, a plurality of Xs being the same as or different from one another, and when there is X bonding to a carbon atom in γ-position of a carbonyl group, at least one X bonding to a carbon atom in γ-position being a hydrogen atom, Y represents a hydrogen atom or a methyl group, p represents an integer of at least 1 and no greater than 3, q represents an integer of at least 0 and no greater than 3, and r represents 1 or 2.

2. The pretreatment solution for inkjet recording according to claim 1, wherein in the general formulas (I) and (II), $R^1$ represents an alkyl group having a carbon number of at least 1 and no greater than 5, or a fluoroalkyl group having a carbon number of at least 1 and no greater than 5, $R^2$ represents an aryl group having a carbon number of at least 6 and no greater than 14, p represents 2, q represents 1, and r represents 1.

3. The pretreatment solution for inkjet recording according to claim 2, wherein the photoacid generator is a compound represented by chemical formula (II-1) shown below

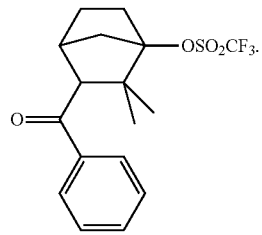

(II-1)

4. The pretreatment solution for inkjet recording according to claim 1, further comprising water and a water-soluble organic solvent.

5. The pretreatment solution for inkjet recording according to claim 1, wherein a content rate of the photoacid generator is at least 0.1% by mass and no greater than 5.0% by mass.

6. An inkjet recording apparatus for forming an image in an image forming region on a recording medium, comprising:

a pretreating section configured to eject the pretreatment solution for inkjet recording according to claim 1 onto the image forming region on the recording medium;

an exposing section configured to expose, to light, the image forming region on the recording medium onto which the pretreatment solution for inkjet recording has been ejected; and a recording head configured to form the image by ejecting an ink onto the exposed image forming region on the recording medium.

7. An image forming method for forming an image in an image forming region on a recording medium, comprising:

ejecting the pretreatment solution for inkjet recording according to claim 1 onto the image forming region on the recording medium;

exposing, to light, the image forming region on the recording medium on which the pretreatment solution for inkjet recording has been ejected; and forming the image by ejecting an ink onto the exposed image recording region on the recording medium.

* * * * *